United States Patent
Song et al.

(10) Patent No.: US 9,416,196 B2
(45) Date of Patent: Aug. 16, 2016

(54) COMPOSITION FOR PROPHYLAXIS OR TREATMENT OF VASCULAR OR CARDIAC VALVULAR CALCIFICATION COMPRISING DIPEPTIDYL PEPTIDASE-4 INHIBITOR

(71) Applicant: THE ASAN FOUNDATION, Seoul (KR)

(72) Inventors: Jae Kwan Song, Seoul (KR); Eun Ju Chang, Seoul (KR); Mi Jeong Kim, Incheon (KR); Bongkun Choi, Gyeonggi-do (KR); Sahmin Lee, Seoul (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 8 days.

(21) Appl. No.: 14/473,618

(22) Filed: Aug. 29, 2014

(65) Prior Publication Data

US 2015/0065693 A1 Mar. 5, 2015

(30) Foreign Application Priority Data

Aug. 29, 2013 (KR) ......................... 10-2013-0103189

(51) Int. Cl.
- A61K 31/70 (2006.01)
- C07K 16/44 (2006.01)
- A61K 31/4985 (2006.01)
- A61K 31/7105 (2006.01)
- A61K 31/713 (2006.01)
- A61K 38/06 (2006.01)
- C12N 5/00 (2006.01)

(52) U.S. Cl.
CPC ............. *C07K 16/44* (2013.01); *A61K 31/4985* (2013.01); *A61K 31/713* (2013.01); *A61K 31/7105* (2013.01); *A61K 38/06* (2013.01); *C12Y 304/14005* (2013.01)

(58) Field of Classification Search
None
See application file for complete search history.

(56) References Cited

U.S. PATENT DOCUMENTS

| 2013/0196998 A1* | 8/2013 | Stoit | C07D 265/36 514/238.8 |
| 2013/0303554 A1* | 11/2013 | Klein | A61K 31/522 514/263.21 |

FOREIGN PATENT DOCUMENTS

KR   1020110115582 A   10/2011

OTHER PUBLICATIONS

Atochin, Dimitriy N. et al., "Rapid cerebral ischemic preconditioning in mice deficient in endothelial and neuronal nitric oxide synthases", Stroke. 2003; pp. 1299-1303; vol. 45, originally published online Apr. 3, 2003.

Atochin, Dmitriy N. et al., "Endothelial nitric oxide synthase transgenic models of endothelial dysfunction", Pflugers Arch—Eur J. Physiol, Nov. 2010; 460(6); pp. 965-974.

Atochin, Dmitriy N. et al., "The phosphorylation state of eNOS modulates vascular reactivity and outcome of cerebral ischemia in vivo", J. Clin. Invest. 117, pp. 1961-1967 (2007).

Bredt, David S. et al., "Isolation of nitric oxide synthetase, a calmodulin-requiring enzyme", Proc. Natl. Acad. Sci. USA, vol. 87, pp. 682-685, Jan. 1990.

Bucay, Nathan et al., "Osteoprotegerin-deficient mice develop early onset osteoporosis and arterial calcification", Genes Dev., 1998 12, pp. 1260-1268.

Cho, Hyun-Ju et al., "Vascular calcifying progenitor cells possess bidirectional differentiation potentials", PLoS Biol 11(4): e1001534.

Cohen, Jr., M. M. et al., "The new bone biology: pathologic, molecular, and clinical correlates", Am J Med Genet Part A 2006;140A: pp. 2646-2706.

Collin-Osdoby, Patricia, "Regulation of vascular calcification by osteoclast regulatory factors RANKL and osteoprotegerin", Circ Res., 2004; 95, pp. 1046-1057.

Eggen, Douglas A. et al., "Coronary calcification. Relationship to clinically significant coronary lesions and race, sex, and topographic distribution", Circulation J. of the Amer. Heart Assoc., 1965; 3, pp. 948-955.

Fadini, Gian P. et al., "Emerging role of circulating calcifying cells in the bone-vascular axis", Circulation, Jun. 5, 2012; 125(22), pp. 2772-2781.

Feng, Qingping et al., "Development of heart failure and congenital septal defects in mice lacking endothelial nitric oxide synthase", Circulation, 2002; 106, pp. 873-879; originally published online Jul. 22, 2002.

Fleischer, B., "CD26: a surface protease involved in T-cell activation", Immunol Today, 1994; 15, pp. 180-184.

Freedman, Jane E. et al., "Deficient platelet-derived nitric oxide and enhanced hemostasis in mice lacking the NOSIII gene", Circ Res., 1999; 84, pp. 1416-1421.

Furchgott, R. F. et al., "The obligatory role of endothelial cells in the relaxation of arterial smooth muscle by acetylcholine", Nature, 1980; 288, pp. 373-376.

Gimbrone, Jr., Michael A. et al., "Endothelial dysfunction and atherosclerosis", J Card Surg, 1989; 4, pp. 180-183.

Godecke, Axel et al., "Coronary hemodynamics in endothelial NO synthase knockout mice", Circ Res, 1998; 82, pp. 186-194.

Haynes, M. P. et al., "Membrane estrogen receptor engagement activates endothelial nitric oxide synthase via the PI3-kinase-akt pathway in human endothelial cells", Circ Res, 2000; k87, pp. 677-682.

(Continued)

*Primary Examiner* — Sean McGarry (74) *Attorney, Agent, or Firm* — Hultquist, PLLC; Steven J. Hultquist (57) ABSTRACT

There is provided a composition for prophylaxis or treatment of vascular or valvular calcification including a dipeptidylpeptidase-4 (DPP-4) inhibitor. The DPP-4 according to one exemplary embodiment of the present disclosure is expressed at an increased level when blood vessels and valves are calcified, and the calcification decreases remarkably upon administration of the DPP-4 inhibitor. Therefore, the DPP-4 inhibitor can be useful in treatment or prophylaxis of blood vessels or valves.

5 Claims, 11 Drawing Sheets

(56) References Cited

OTHER PUBLICATIONS

Hopsu-Havu, V. K. et al., "A new dipeptide naphthylamidase hydrolyzing glycyl-prolyl-beta-naphthylamide", Histochimie, 1966, 7, pp. 197-201.
Huang, P. L. et al., "Hypertension in mice lacking the gene for endothelial nitric oxide synthase", Nature, 1995, 377, pp. 239-242.
Huang, P. L., "Lessons learned from nitric oxide synthase knockout animals", Semin Perinatol, 2000, 24, pp. 87-90.
Jonk, A. M. et al., "Microvascular dysfunction in obesity: a potential mechanism in the pathogenesis of obesity-associated insulin resistance and hypertension", Physiol., 2007, 22, pp. 252-260.
Jose, Tessey et al., "Cardiovascular effects of the DPP-4 inhibitors", Diab Vasc Dis Res., 2012, 9, pp. 109-116, originally published online Feb. 15, 2012.
Kelly, Ralph A. et al., "Nitric oxide and cardiac function", Circ Res., 1996; 79, pp. 363-380.
Korom, S. et al., "Inhibition of CD26/dipeptidyl peptidase IV activity in vivo prolongs cardiac allograft survival in rat recipients", Transplantation 1997, 63, pp. 1495-1500.
Kyle, Kimberly A. et al., "Differential effects of PPAR-γ activation versus chemical or genetic reduction of DPP-4 activity on bone quality in mice", Endocrinol 2011, 52, pp. 457-467.
Lampropoulos, Christos E. et al., "Osteoporosis—a risk factor for cardiovascular disease?", Nat Rev Rheumatol 2012, 8, pp. 587-598.
Lee, Tony C. et al., "Abnormal aortic valve development in mice lacking endothelial nitric oxide synthase", Circulation 2000, 101, pp. 2345-2348.
Lefer, David J. et al., "Leukocyte-endothelial cell interactions in nitric oxide synthase-deficient mice", Am J Physiol 1999, 276, pp. H1943-H1950.
Lenski, M. et al., "Effects of DPP-4 inhibition on cardiac metabolism and function in mice", J Mol Cell Cardiol 2011, 51, pp. 906-918.
Lo, Eng H. et al., "Temporal Correlation Mapping Analysis of the Hemodynamic Penumbra in Mutant Mice Deficient in Endothelial Nitric Oxide Synthase Gene Expression", Stroke 1996, 27, pp. 1381-1385.
Marguet, Didier et al., "Enhanced insulin secretion and improved glucose tolerance in mice lacking CD26", Proc Natl Acad Sci USA 2000, 97, pp. 6874-6879.
Moens, A. L. et al., "Flow-mediated vasodilation: a diagnostic instrument, or an experimental tool?", Chest 2005, 127, pp. 2254-2263.
Mungrue, I. N. et al., "The role of NOS in heart failure: lessons from murine genetic models", Heart Fail Rev 2002, 7, pp. 407-422.
Myers, Paul R. et al., "Vascular endothelial cell regulation of extracellular matrix collagen: role of nitric oxide", Arterioscler Thromb Vasc Biol. 1998, 18, pp. 717-722.
Nisoli, Enzo et al., "Defective mitochondrial biogenesis: a hallmark of the high cardiovascular risk in the metabolic syndrome?", Circ Res. 2007, 100, pp. 795-806.
Nisoli, Enzo et al., "Effects of nitric oxide on proliferation and differentiation of rat brown adipocytes in primary cultures", Br J Pharmacol 1998, 125, pp. 888-894.
Ohnuma, K. et al., "Revisiting an old acquaintance: CD26 and its molecular mechanisms in T cell function", Trends Immunol 2008, 29, pp. 295-301.
Pollack, J. S. et al., "Purification and characterization of particulate endothelium-derived relaxing factor synthase from cultured and native bovine aortic endothelial cells", Proc Natl Acad Sci USA 1991, 88, pp. 10480-10484.
Potente, Michael, "An energy-sensor network takes center stage during endothelial aging", Circ Res. 2010, 106, pp. 1316-1318.
Rajamannan, N. M. et al., "Atorvastatin inhibits calcification and enhances nitric oxide synthase production in the hypercholesterolaemic aortic valve", Heart 2005, 91, pp. 806-810.
Rask-Madsen, Christian et al., "Insulin therapy improves insulin-stimulated endothelial function in patients with Type 2 diabetes and ischemic heart disease", Diabetes 2001, 50, pp. 2611-2618.
Sage, Andrew P. et al., "Regulatory mechanisms in atherosclerotic calcification", Nat Rev Cardiol. Sep. 2010; 7(9): pp. 528-536.
Sallam, T. et al., "Regulatory circuits controlling vascular cell calcification", Cell Mol Life Sci Sep. 2013 70(17), pp. 3187-3197.
Serne, Erik H. et al., "Microvascular dysfunction: a potential pathophysiological role in the metabolic syndrome", Hypertens 2007, 50, pp. 204-211.
Shao, Jian-Su et al., "Inflammation and the osteogenic regulation of vascular calcification: a review and perspective", Hypertension. Mar. 2010; 55(3), pp. 579-592.
Simmons, Craig A. et al., "Spatial heterogeneity of endothelial phenotypes correlates with side-specific vulnerability to calcification in normal porcine aortic valves", Circ Res. 2005, 96, pp. 792-799; originally published online Mar. 10, 2005, and 24 pages of supplemental content.
Steinbrecher, Andreas et al., "Targeting Dipeptidyl Peptidase IV (CD26) Suppresses Autoimmune Encephalomyelitis and Up-Regulates TGF-β1 Secretion In Vivo", J Immunol 2001; 166, pp. 2041-2048.
Stewart, B. F. et al., "Clinical Factors Associated With Calcific Aortic Valve Disease", J Am Coll Cardiol 1997;29, pp. 630-634.
Tanaka, S. et al., "Suppression of arthritis by the inhibitors of dipeptidyl peptidase IV", Int J. Immunopharmacol 1997, 19, pp. 15-24.
Tanaka, T. et al., "Cloning and functional expression of the T cell activation antigen CD26", J Immunol 1992, 149, pp. 481-486.
Ussher, John R. et al., "Cardiovascular Biology of the Incretin System", Endocr Rev. Apr. 2012; 33(2), pp. 187-215.
Uzzan, B. et al., "Effects of statins on bone mineral density: a meta-analysis of clinical studies", Bone 2007, 40, pp. 1581-1587.
Widlandsky, Michael E. et al., "The clinical implications of endothelial dysfunction", J Am Coll Cardiol 2003, 42, pp. 1149-1160.
Xie, D. et al., "Glucose-dependent insulinotropic polypeptide receptor knockout mice have altered bone turnover", Bone 2005, 37, pp. 759-769.
Yip, Cindy Y. et al., "Inhibition of pathological differentiation of valvular interstitial cells by C-type natriuretic peptide", Arterioscler Thromb Vasc Biol. 2011, 31, pp. 1881-1889; originally published online May 26, 2011, and 12 pages of supplemental material.
Yui, Yoshiki et al., "Purification of nitric oxide synthase from rat macrophages", The Journal of biological chemistry 1991, 266, pp. 12544-12547.
Zhao, X. et al., "Deficiency in endothelial nitric oxide synthase impairs myocardial angiogenesis", Am J Physiol Heart Circ Physio, 2002, 283, pp. H2371-H2378.
Zhong, Qing et al., "Effects of glucose-dependent insulinotropic peptide on osteoclast function", Am J Physiol Endocrinol Metab 2007, 292, pp. E543-E548, First published Sep. 26, 2006.
Dweck, M., et al., "Aortic stenosis, atherosclerosis, and skeletal bone: is there a common link with calcification and inflammation?", "European Heart Journal", Feb. 7, 2013, pp. 1567-1574, vol. 34, No. 21.
Rossebo, A., et al., "Intensive lipid lowering with simvastatin and ezetimibe in aortic stenosis.", "New England Journal of Medicine", Sep. 2, 2008, pp. 1343-1356, vol. 359, No. 13.
Nguyen, N., et al., "Diabetes mellitus accelerates cartilaginous metaplasia and calcification in atherosclerotic vessels of LDLr mutant mice", "Cardiovascular Pathology", Jul. 8, 2012, pp. 167-175, vol. 22, No. 2.

* cited by examiner

COMPOSITION FOR PROPHYLAXIS OR TREATMENT OF VASCULAR OR CARDIAC VALVULAR CALCIFICATION COMPRISING DIPEPTIDYL PEPTIDASE-4 INHIBITOR

CROSS-REFERENCE TO RELATED APPLICATION

This application claims the benefit of Korean Patent Application No. 10-2013-0103189 filed on Aug. 29, 2013, with the Korean Intellectual Property Office, the disclosure of which is incorporated herein by reference.

BACKGROUND

The present disclosure relates to a composition for prophylaxis or treatment of vascular or valvular calcification including a dipeptidyl peptidase-4 (DPP-4) inhibitor.

Cardiovascular calcification contributes to exacerbation of hypertension, heart failure, acute coronary syndrome, and valvular diseases, and thus causes various complications. Also, a variety of epidemiological studies have found that vascular calcification independently increases the mortalities. Vascular calcification occurs in a mechanism similar to an osteogenic program after a normal prenatal stage or a bone fracture, and is activated in diseases such as old age, diabetes, chronic renal failure, chronic inflammatory diseases. The loss of minerals in bones is accelerated by an inflammatory response, and the free minerals are endocytosed into abnormal vascular endothelial cells.

Vascular endothelial dysfunction is an important mechanism for vascular calcification. Normally, endothelial nitric oxide synthase (eNOS) is constitutively expressed at a certain level in vascular endothelial cells, endomyocardial cells, atrial cells, vascular smooth muscle cells, respiratory endothelial cells, and the like, and serves to adjust a vascular tone and maintain homeostasis of vascular endothelial cells by forming nitric oxide (NO). When the dysfunction of eNOS appears, isoenzymes, such as neuronal NOS (nNOS) or inducible NOS (iNOS), which have structures and functions similar to the eNOS, increase compensatorily to replace the role of eNOS, but do not continuously maintain normal vascular endothelial cell functions with ease. Therefore, pathologic alterations in blood vessels including atherosclerosis occur at an early stage. In a laboratory animal model studying an effect of endothelial nitric oxide synthase (eNOS) on the cardiovascular system, that is, an endothelial nitric oxide synthase knockout (eNOS KO) animal model, it was known that the onset of hypertension and atherosclerosis increases, and wide lesional areas and severe remodeling occur after apoplexy and myocardial infarction, compared to the control.

The present inventors have made an ardent effort to elucidate a cardiovascular calcification procedure and develop a therapeutic drug for cardiovascular calcification, and found that DPP-4 is expressed at an increased level in an animal model in which the cardiovascular calcification is induced, and an inhibitor of DPP-4 effectively inhibits calcification of blood vessels and valves. Therefore, the present disclosure has been completed based on these facts.

SUMMARY

An aspect of the present disclosure may provide a pharmaceutical composition for prophylaxis or treatment of vascular or valvular calcification including a dipeptidyl peptidase-4 (DPP-4) inhibitor.

Another aspect of the present disclosure may provide a food composition for prophylaxis or improvement of vascular or valvular calcification including a DPP-4 inhibitor.

According to an aspect of the present disclosure, a composition for prophylaxis or treatment of vascular or valvular calcification may include a DPP-4 inhibitor.

The composition may include a pharmaceutical composition, or a food composition.

Hereinafter, the present disclosure will be described in further detail.

According to one exemplary embodiment of the present disclosure, DPP-4 is also designated as a cluster of differentiation 26 (CD26), and is known to be a protein associated with immune modulation, apoptosis, signal transduction, and the like.

For the composition according to one exemplary embodiment of the present disclosure, the DPP-4 inhibitor may be either an inhibitor for inhibiting expression of a DPP-4 nucleotide sequence or an inhibitor for inhibiting the activity of a DPP-4 protein. The inhibitor for inhibiting the expression of the DPP-4 nucleotide sequence may, for example, include an antisense nucleotide sequence against mRNA of the DPP-4, an aptamer, small interfering RNA (siRNA), short hairpin RNA (shRNA), micro RNA (miRNA), or RNA interference (RNAi).

Also, the inhibitor for inhibiting the activity of the DPP-4 protein may, for example, include an antibody against DPP-4, sitagliptin, vildagliptin, saxagliptin, linagliptin, dutogliptin, gemigliptin, alogliptin, anagliptin, berberine, diprotin, lupeol, Evogliptin, Omarigliptin, teneligliptin, or trelagliptin. In the present disclosure, the DPP-4 may be a monoclonal antibody, or a polyclonal antibody.

In the present disclosure, the DPP-4 is expressed at an increased level when blood vessels and valves are calcified, and the calcification decreases remarkably upon administration of the DPP-4 inhibitor. Therefore, the DPP-4 inhibitor can be useful in treatment or prophylaxis of the blood vessels or the valves.

According to one exemplary embodiment of the present disclosure, the vascular or valvular calcification refers to formation, growth and deposition of extracellular matrix hydroxyapatite (calcium phosphate) crystal deposits in the blood vessels or valves. The vascular calcification encompasses calcification of coronary arteries, aorta, and other blood vessels.

The calcification includes medial calcification, or atherosclerotic calcification. A calcified tissue is referred to as a calcified cartilage. Intimal calcification occurs in connection with atherosclerosis. In the case of atherosclerosis, fat-rich macrophagocytes and T lymphocytes are first accumulated in blood vessels or valves to form a layer of fat, and smooth muscle cells then migrate from the media into the layer of fat. Chemokinetic compounds stimulating the movement of such cells are considered to be produced in proximal endothelial cells, activated phagocytes, and the like. The migrated smooth muscle cells proliferate, fats are accumulated in the smooth muscle cells, and extracellular matrices are formed. The calcification occurs at the central region of an artheromatous plaque. The medial calcification occurs regardless of atherosclerosis and intimal calcification. The medial arterial calcification occurring at the distal arteries is also referred to as Monckeberg's sclerosis, and is often observed in the aged diabetic patients. It was known that smooth muscle cells and elastin are associated with the occurrence of the medial arterial calcification.

In the present disclosure, the term "atherosclerotic calcification" refers to vascular calcification occurring in artheromatous plaques along the intima.

In the present disclosure, the medial calcification, the medial wall calcification, or the Monckeberg's sclerosis refers to calcification characterized by the presence of calcium in the medial wall.

Also, the calcification according to one exemplary embodiment of the present disclosure may be caused by a valvular disease, hyperlipidaemia, senility, estrogen deficiency, angina, heart failure, nephritis, uremia, diabetes, an inflammatory disease, or a cardiovascular disorder. Examples of the nephritis may include glomerulonephritis, diabetic nephritis, lupus nephritis, multiple pustular nephritis, pyelonephritis, lithonephria, nephrotuberculosis, renal tumor, and the like. Also, examples of the inflammatory disease may include asthma, allergic and non-allergic rhinitis, chronic and acute rhinitis, chronic and acute gastritis or enteritis, ulcerative gastritis, acute and chronic nephritis, acute and chronic hepatitis, a chronic obstructive pulmonary disease, pulmonary fibrosis, an irritable bowel syndrome, inflammatory pain, migraine headache, headache, backache, a fibromyalgia syndrome, a myofascial disease, a viral infection (for example, hepatitis C), a bacterial infection, a fungal infection, a burn, an injury caused by a surgical or dental operation, a prostaglandin E overload syndrome, atherosclerosis, gout, arthritis, rheumatic arthritis, ankylosing spondylitis, a Hodgkin's disease, pancreatitis, conjunctivitis, iritis, scleratitis, uveitis, dermatitis, eczema, or multiple sclerosis. In addition, examples of the cardiovascular disease may include myocardiopathy, a primary cardiac arrest, ischemic heart failure, hypertension, an ischemic heart disease, a coronary artery disease, angina, myocardial infarction, atherosclerosis, or arrhythmia.

The pharmaceutical composition according to one exemplary embodiment of the present disclosure may further include a pharmaceutically available carrier. The pharmaceutically available carrier may include a saline solution, sterile water, a Ringer's solution, a buffered saline solution, dextrose solution, maltodextrin solution, glycerol, ethanol and a mixture thereof, which may be used alone or in combination. When necessary, other conventional additives such as an antioxidant, a buffer and a bacteristat may be added to the composition. Also, a diluent, a dispersing agent, a surfactant, a binding agent and a lubricating agent may be further added to the composition. In this case, the composition may be formulated into an injectable formulation such as an aqueous solution, a suspension, or an emulsion, a pill, a capsule, a granule, or a tablet. In addition, the pharmaceutical composition may be preferably formulated according to individual diseases and components using a proper method known in the related art, or a method disclosed in Remington's Pharmaceutical Science (recent Version), Mack Publishing Company, Easton Pa. Examples of the pharmaceutically available carriers, the formulations of the pharmaceutical composition, and methods of preparing the formulations are known in the related art.

Also, such pharmaceutical compositions may be useful in administering a composition including the DPP-4 inhibitor according to one exemplary embodiment of the present disclosure as an active ingredient to a subject so as to treat the vascular or valvular calcification, as described above. The composition according to one exemplary embodiment of the present disclosure may be provided at an effective amount to treat the vascular or valvular calcification in the subject in need.

The dose of the DPP-4 inhibitor may vary to a wide extent according to the body weight, age, gender and health condition of a patient, a diet, an administration time, a method of administration, an excretion rate, and the severity of a disease. In this case, the dose of the DPP-4 inhibitor may be optionally determined by those skilled in the related art, for example, about 0.00001 to 5,000 mg/kg, and may be administered once a day, or administered in divided doses.

The composition according to one exemplary embodiment of the present disclosure may be administered orally, or parenterally ((for example, intravenously, subcutaneously, intraperitoneally, intramuscularly, intravascularly, or subcutaneously) according to a desired purpose. Preferably, the composition may be administered orally. For oral administration, the composition may be provided in the form of a capsule, a tablet, a powder, a granule, or a suspension. Also, the formulation may include a conventional additive such as lactose, mannitol, corn starch, or potato starch, and the binding agent that may be used in such formulations may include crystalline cellulose, cellulose analogue, acacia, corn starch, or sodium carboxymethyl cellulose.

Also, the formulations may be provided with dibasic calcium phosphate, or anhydrous sodium starch glycolate. Finally, the formulations may be provided with a lubricating agent, for example, talc or magnesium stearate.

Further, the composition according to one exemplary embodiment of the present disclosure may be used alone or in combination with surgery, hormone treatment, drug treatment, and methods using a biological response modifier in order to prevent or treat the vascular or valvular calcification.

The food composition for prophylaxis or improvement of vascular or valvular calcification according to one exemplary embodiment of the present disclosure is not particularly limited to the formulations. Examples of foods to which the composition may be added may include meat, sausage, bread, chocolate, candies, snacks, confectionery, pizza, ramen or other noodles, gums, dairy products including ice creams, various soups, beverages, tea, drinks, alcoholic beverages, and vitamin complexes. In this case, the foods encompass all kinds of health foods in a conventional aspect.

In addition to the DPP-4 inhibitor that may be included in the food composition according to one exemplary embodiment of the present disclosure, other components that may be further included in the food composition are not particularly limited. For example, the food composition may further include various herbal extracts such as conventional foods, food supplements, or natural carbohydrates as additional components. Also, the food composition may further include a food supplement. In this case, the food supplement includes a fragrance, a flavoring agent, a coloring agent, a filler, a stabilizing agent, and the like, all of which are widely used in the related art. Examples of the natural carbohydrates may include typical sugars such as monosaccharides, for example, glucose, fructose, and the like; disaccharides, for example maltose, sucrose, and the like; and polysaccharides, for example dextrin, cyclodextrindextrin, and the like, and sugar alcohols such as xylitol, sorbitol, erythritol, and the like. In addition to the above-described components, a natural fragrance (i.e., thaumatin, a stevia extract (for example rebaudioside A, glycyrrhizin, etc.)), and a synthetic fragrance (i.e., saccharin, aspartame, etc.) may be desirably used as the fragrance. In addition, the food composition of the present invention may contain various nutrients, vitamins, minerals (electrolytes), a flavoring agent such as a synthetic flavoring agent, a natural flavoring agent, etc., a coloring agent, an extender (cheese, chocolate, etc.), pectic acid and a salt thereof, alginic acid and a salt thereof, organic acid, a protective colloid thickener, a PH adjuster, a stabilizing agent, a preservative, glycerin, alcohol, a carbonating agent used for a carbonated drink, etc. In addition, the food composition of the present invention may include flesh that may be used for preparing natural fruit juice, fruit juice drinks, and vegetable drinks. Such components may be used alone or in combination.

BRIEF DESCRIPTION OF DRAWINGS

The above and other aspects, features and other advantages of the present disclosure will be more clearly understood from the following detailed description taken in conjunction with the accompanying drawings, in which.

DETAILED DESCRIPTION

Exemplary embodiments of the present disclosure will now be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

In the drawings, the shapes and dimensions of elements may be exaggerated for clarity, and the same reference numerals will be used throughout to designate the same or like elements.

Example 1

Treatment of Animal Model eNOS KO mice (n=10, The Jackson Laboratory, Bar Harbor, Me., USA) derived from D C57BL/6J, and homogeneous wild-type control mice (wide type, WT, n=10) were used. After the mice were brought in here, the standard rodent feed was provided until the mice were 3 month old. Then, the high-fat diet (Purina Mills, Woodmont, Ind., USA) was provided for 6 months. Besides the diet, the mice were raised according to the typical animal care guidelines. On the time point of $9^{th}$ month, the mice were anesthetized by deeply injecting 1.2% 2,2,2-tribromoethanol into the abdominal cavities of the mice, and the blood and tissues were taken while the mice were anesthetized. The blood was drawn using a glass capillary tube, and then centrifuged to obtain a supernatant of plasma, which was stored at $-80°$ C. The mice were sacrificed by injecting 0.1 mL of pentobarbital/phenyloin into the mouse hearts, and the hearts and ascending aortas were extracted. Soft tissues were removed from the extracted tissues, and the extracted tissues were rinsed with a physiological saline solution. Thereafter, the ascending aortas were separated from the tissues, and each heart was divided into three parts: an apical region, a middle region, and a basal region including the aortic valves. The apical region was quick-frozen at $-80°$ C. with liquid nitrogen in order to prevent a sudden change in phosphorylated state. The middle and basal regions of the heart were fixed in a 4% formalin solution for 24 hours, embedded into paraffin, and then microtomed into fragments having a thickness of 4 mm.

Example 2

Separation and Culturing of Vascular Smooth Muscle Cells

The aorta extracted with the heart was washed with a serum-free M199 medium (Cellgro), and cut into small pieces. Thereafter, 20% fetal calf serum, and 3 mg/mL collagenase (Sigma) were added to the M199 medium, and boiled for 3 hours in a 37° C. water bath. Then, it was confirmed that the separated cells were vascular smooth muscle cells using an α-SM actin monoclonal antibody (Sigma). The separated vascular smooth muscle cells were divided at a 30% concentration, and the medium used was replaced with osteogenic medium (Osteogenic Basal Medium, Osteogenic Single-Quots, Lonza, USA) after 24 hours. The medium was replaced every 3 days, and the cell culture was performed for 28 days. The concentration of sCD26/DPP-4 was measured upon medium replacement.

The measured value was represented by the average±standard deviation, and difference in two individual groups was assayed using a Student t-test and a Mann-Whitney test. The difference was considered to be statistically significant when P<0.05.

Example 3

Determination of Occurrence of Aortic Valvular Calcification in eNOS KO Mice

To determine the occurrence of aortic valvular calcification in eNOS KO mice, tissue staining was performed.

More particularly, the tissues were stained with a von Kossa stain and a Alizarin red stain in order to determine calcium deposition in the fragments of the aortic valve and the heart basal region embedded into paraffin. The von Kossa staining was performed by washing the formalin-fixed aortic valve with distilled water and exposing the aortic valve to 5% water-soluble $AgNO_3$ and strong light at room temperature for 60 minutes. Thereafter, when the aortic valve was treated with 2.5% sodium thiosulfate for 5 minutes and turned blackish brown, this staining was evaluated to be positive. The Alizarin red staining was evaluated to be positive when the formalin-fixed aortic valve turned red or orange after the aortic valve was washed with distilled water and then treated with 2% Alizarin red S (aqueous, Sigma) for 5 minutes.

Also, the alkaline phosphatase activity was measured to determine the presence of osteogenic cells. When a tissue slide turned dark grey to brown after the tissue slide was dipped in a nitroblue tetrazolium chloride/5-bromo-4-choloro-3-indolyl phosphate toluidine salt (NBT/BCIP) solution at room temperature for 10 minutes, washed with distilled water, and then dried, the alkaline phosphatase activity was evaluated to be positive.

Figure 1:
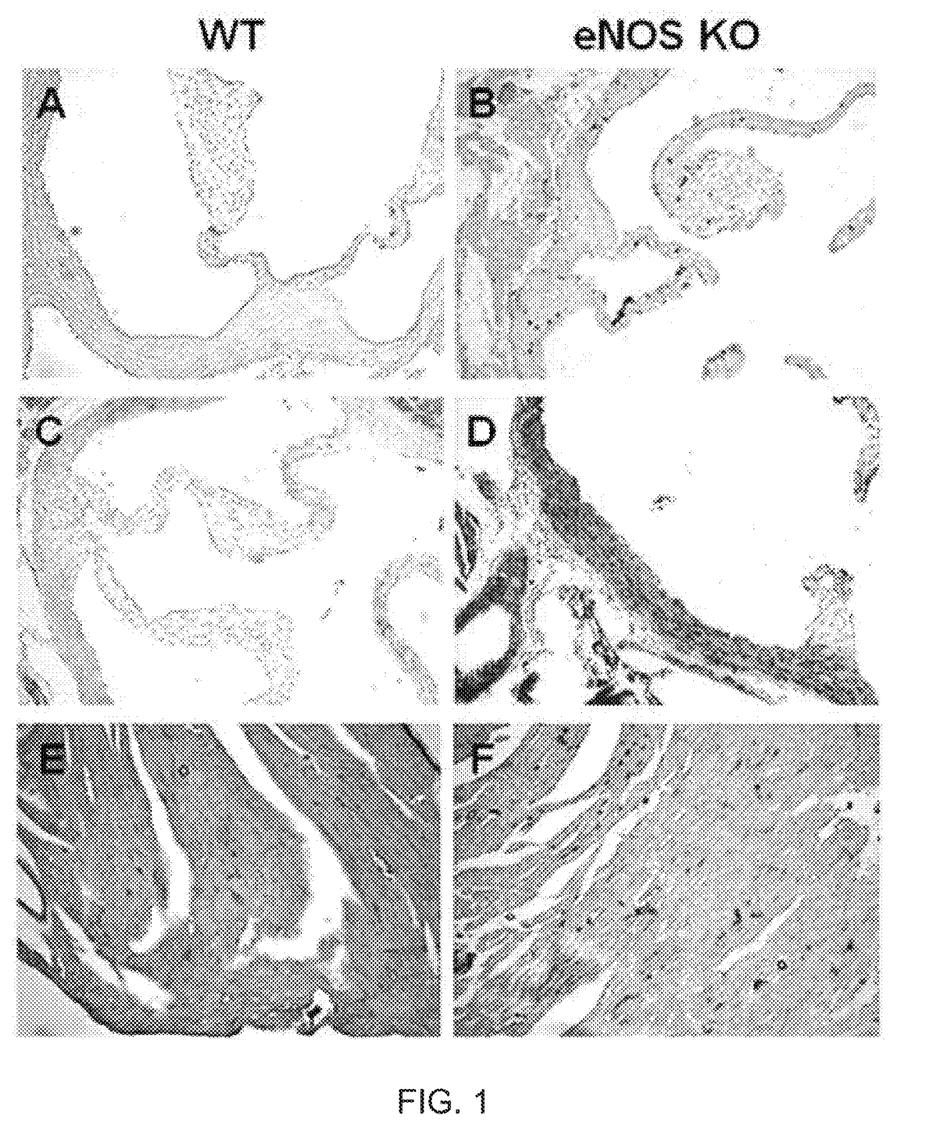
FIG. 1 is a diagram showing the tissue staining results of aortic valves in eNOS KO mice according to one exemplary embodiment of the present disclosure.

To determine the vascular pathologies in the control (WT) and eNOS KO mice, the tissue staining results were compared. The results are shown in FIG. 1. FIGS. 1A and 1B show the staining of the aortic valve with a von Kossa stain (×200), FIGS. 1C and 1D show the staining of the aortic valve and aortic root with an Alizarin red stain (×200), and FIGS. 1E and 1F show the staining of the staining of the aorta with an alkaline phosphatase stain (×200).

As shown in FIG. 1, it was revealed that a region stained blackish brown, which indicated the mineral deposition, was observed in the aortic valves of the eNOS KO mice rather than the control when the aortic valves were stained with the von Kossa stain (FIG. 1B), and a region stained red, which indicated the calcium deposition, was observed when the aortic valves were stained with the Alizarin red stain (FIG. 1D). In the alkaline phosphatase staining performed to determine the presence of the osteogenic cells, the strongly stained cells were observed in the aortas of the eNOS KO mice, compared to the control (FIG. 1F).

Example 4

Determination of Increase in Concentration of Blood CD26/DPP-4 in eNOS KO Mice

To determine an increase in concentration of blood CD26/DPP-4 in the eNOS KO mice, the free CD26/DPP-4 concentrations in the vascular and aortic vascular smooth muscle cell culture broths were measured using a typical ELISA kit (Sigma) according to the manufacturer's guideline. The measurement results are shown in FIGS. 2 and 3.

Figure 2:
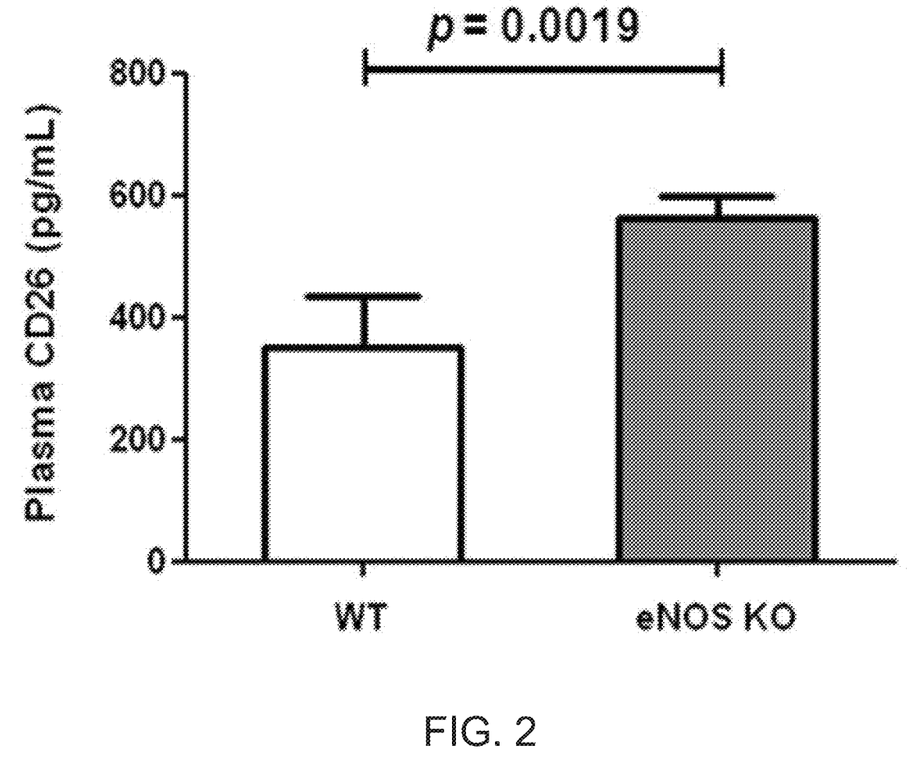
FIG. 2 is a diagram showing the results obtained by comparing the blood CD26/DPP-4 concentrations of the control and eNOS KO mice according to another exemplary embodiment of the present disclosure.
Figure 3:
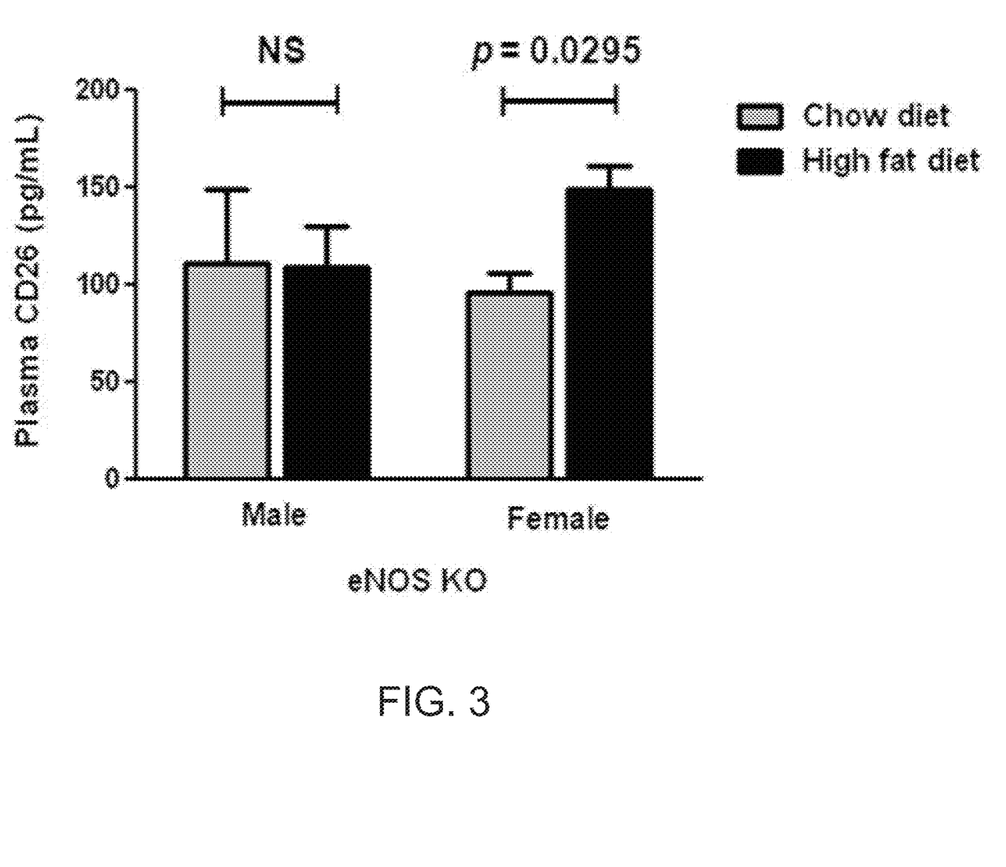
FIG. 3 is a diagram showing the blood CD26/DPP-4 concentrations according to the gender after the high-fat diet for the eNOS KO mice according to still another exemplary embodiment of the present disclosure.

As shown in FIGS. 2 and 3, it was revealed that the blood CD26/DPP-4 (soluble CD26/DPP-4) concentrations were 349.0±84.5 pg/mL and 561.3±38.3 pg/mL for the control and the eNOS KO mice, respectively, indicating that blood CD26/DPP-4 concentration was significantly high in the eNOS KO mice (p=0.0019, FIG. 2). Also, when the mice were provided with a high-fat feed for 6 months, the blood CD26/DPP-4 concentration of the male eNOS KO mice was 105.8±46.7 pg/mL, indicating that there was no difference with respect to the normal rodent feed-administered group (109.9±27.1 pg/mL). On the other hand, the blood CD26/DPP-4 concentrations of the female eNOS KO mice were 97.8±20.2 pg/mL and 143.0±26.0 pg/mL for the normal feed-administered group and the high-fat feed-administered group, respectively, indicating that the blood CD26/DPP-4 concentration was significantly high in the high-fat feed-administered group (p=0.0295, FIG. 3). That is, when the high-fat feed was supplied to the eNOS KO mice, a significant increase in the CD26/DPP-4 concentration was observed in the female mice, compared to the male mice.

Example 5

Determination of Effect of NO on CD26/DPP-4 Expression

To determine an effect of NO on CD26/DPP-4 expression, a reverse transcription polymerase chain reaction (RT-PCR) was used.

More particularly, the total RNA was separated from each of the aortas of the control and the eNOS KO mice using an ISOGEN kit (Nippon Gene, Toyama, Japan), and the RNA concentration was measured using a spectrophotometer. Thereafter, cDNA was obtained using a high-capacity cDNA Archive kit (Applied Biosystems). 5'-nuclease assay PCR was performed using a universal primer (Applied Biosystems), based on the known CD26/DPP-4 sequence, and the mRNA concentration was measured with reference to glyceraldehyde-3-phosphate dehydrogenase (GAPDH). The results are shown in FIG. 4.

Figure 4:
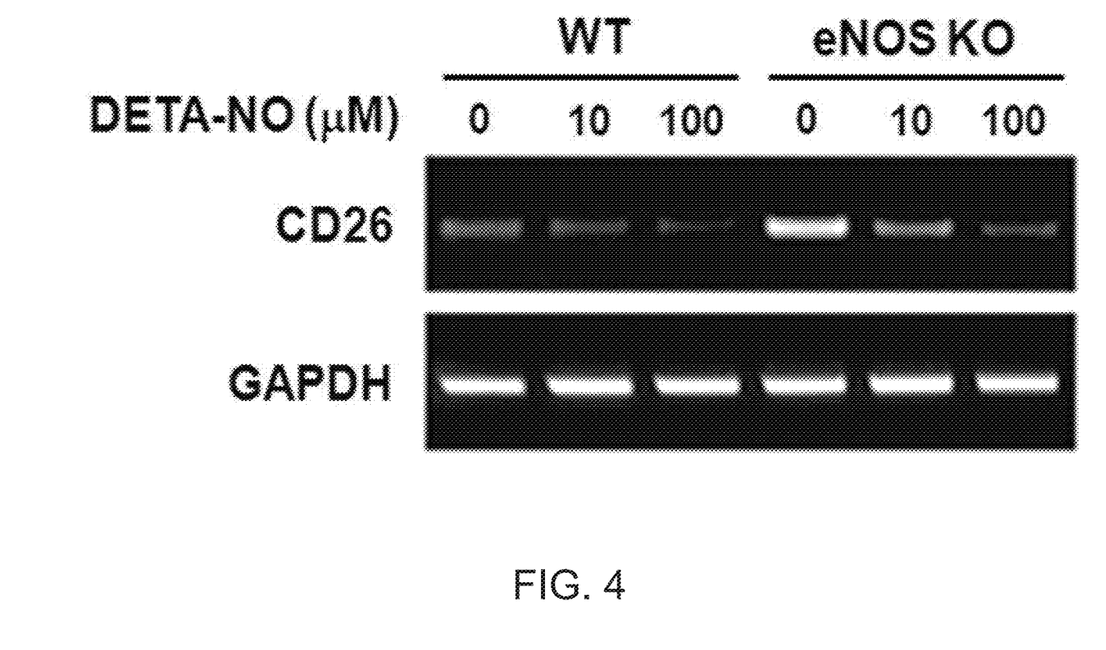
FIG. 4 is a diagram showing the results obtained by determining the role of nitric oxide (NO) on expression of CD26/DPP-4 mRNA according to still another exemplary embodiment of the present disclosure.

As shown in FIG. 4, it was revealed that, when the vascular smooth muscle cells were separated from the aortas of the control and the eNOS KO mice and the RNA expression levels were compared, the expression level of the CD26/DPP-4 mRNA remarkably increased in the vascular smooth muscle cells of the eNOS KO mice, compared to the control. When a NO donor, DETA-NO, was added to the vascular smooth muscle cells, the expression of the CD26/DPP-4 mRNA decreased, the extent of which was in proportion to the concentration of the treated DETA-NO. Therefore, it seemed that the CD26/DPP-4 mRNA expression was induced under a decreased NO condition.

Example 6

Determination of Relationship Between Inflammatory Response and CD26/DPP-4 Expression To examine the role of an inflammatory response in a CD26/DPP-4 expression procedure, the vascular smooth muscle cells were separated from the aortas of the control and the eNOS KO mice, and transfected with a luciferase vector containing a CD26/DPP-4 promoter. Thereafter, the transfected cells were treated with an increasing concentration of an NF-κB inhibitor, and measured for luciferase activity after 24 hours. The results are shown in FIGS. 5 and 6.

Figure 5:
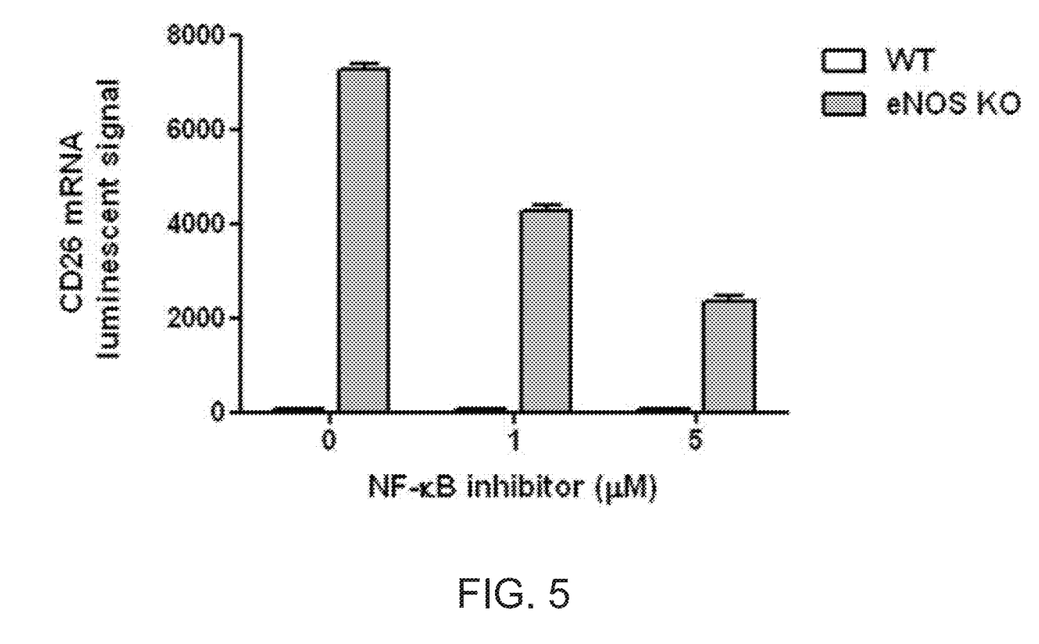
FIG. 5 is a diagram showing the results obtained by determining induction of the expression of CD26/DPP-4 mRNA by a nuclear factor κB (NF-κB) according to still another exemplary embodiment of the present disclosure.

As shown in FIG. 5, it was revealed that a luciferase signal indicating the expression of CD26/DPP-4 mRNA was not detected in the control, but measured at a high level in the eNOS KO mice. In this case, the intensity of the luciferase signal was in inverse proportion to the concentration of the treated NF-κB inhibitor.

Figure 6:
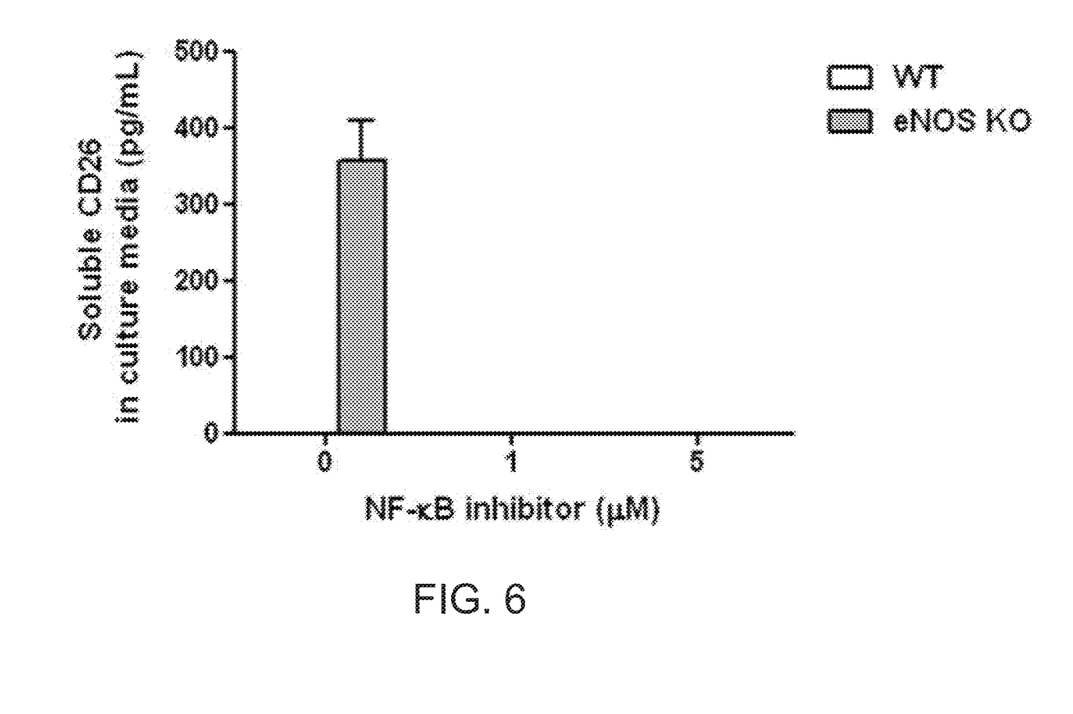
FIG. 6 is a diagram showing the results obtained by determining induction of CD26/DPP-4 by NF-κB according to still another exemplary embodiment of the present disclosure.

Also, as shown in FIG. 6, it was revealed that, when the concentration of soluble CD26/DPP-4 was measured in the culture broth of the separated vascular smooth muscle cells using an ELISA method, the CD26/DPP-4 was not detected in the control, but measured at a high concentration in the culture broth of the cells obtained from the eNOS KO mice. Also, it was revealed that, when the vascular smooth muscle cells were treated with the NF-κB inhibitor, the soluble CD26/DPP-4 concentration remarkably decreased. That is, it seemed that the inflammatory response and the CD26/DPP-4 expression increased in the vascular smooth muscle cells as the NF-κB expression was induced under a NO-deficient or -insufficient condition.

Example 7

Determination of Relationship Between CD26/DPP-4 and Osteogenesis and Mineral Deposition To determine the relationship between the CD26/DPP-4 and the osteogenesis and mineral deposition, the vascular smooth muscle cells were separated from the aortas of the control and the eNOS KO mice, and cultured in an osteogenic medium for 4 weeks. Thereafter, the concentrations of soluble CD26/DPP-4 in the culture broths were measured using an ELISA method. The results are shown in FIG. 7.

Figure 7:
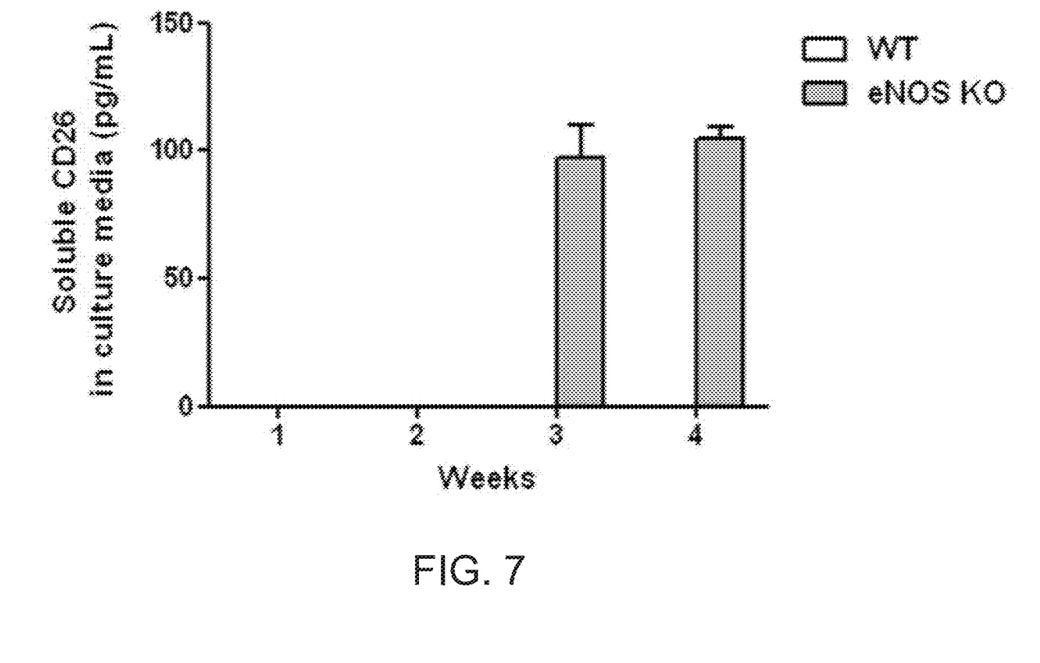
FIG. 7 is a diagram showing the results obtained by determining the expression of CD26/DPP-4 upon osteogenic differentiation of aortic vascular smooth muscle cells according to still another exemplary embodiment of the present disclosure.

As shown in FIG. 7, it was revealed that the CD26/DPP-4 was not detected in the control, but started to be detected at a time point of $3^{rd}$ week of culture in the eNOS KO mice. As a result, it seemed that an inflammatory response occurred under a NO-deficient or -insufficient condition, and thus the CD26/DPP-4 expression was induced, and the vascular smooth muscle cells were differentiated into osteogenic cells in this induction procedure, thereby inducing calcification of blood vessels and valves.

Example 8

Determination of Increase in CD 26 in Aortic Valve Disease Patients

Levels of CD26 in the plasma of normal persons and aortic valve disease (AVD) patients were determined using ELISA. The results are shown in FIG. 8A.

Figure 8:
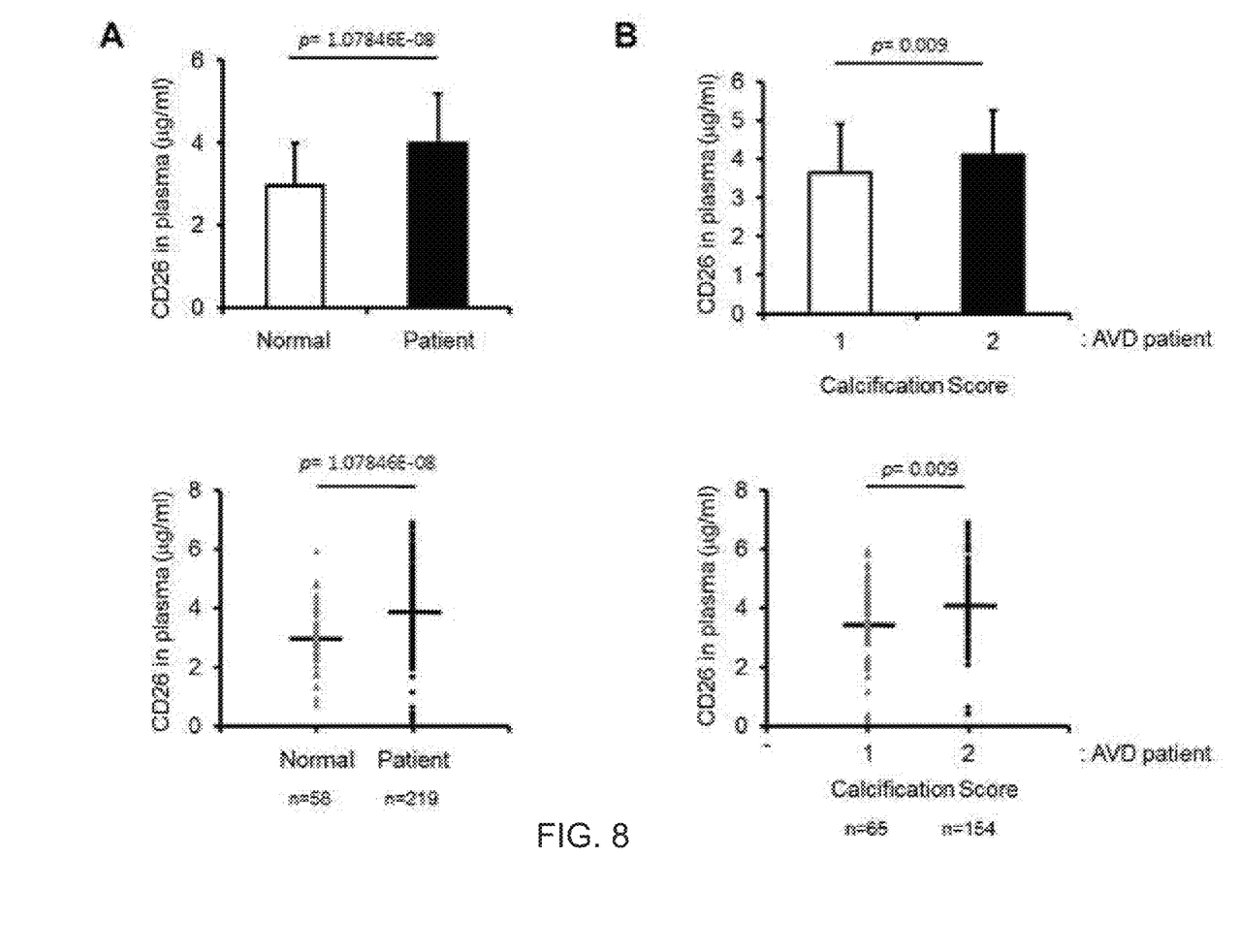
FIG. 8 is a diagram showing the results obtained by determining an increase in plasma CD26 in aortic valve disease patients according to still another exemplary embodiment of the present disclosure.

As shown in FIG. 8A, it was revealed that the CD 26 levels increased in the plasma of the aortic valve disease patients.

Also, the differences in levels of CD26 proteins according to the calcification score of AVD patients and the severity of a disease were compared. The results are shown in FIG. 8B.

As shown in FIG. 8B, it was revealed that the levels of CD26 proteins increased statistically significantly in proportion to the severity of the disease.

Example 9

Determination of Correlation Between Valve Tissue Calcification and CD26 Expression in Aortic Valve Disease Patients To determine the calcification in the heart valves of AVD patients, initial and late calcification procedures were checked using calcium salt deposit staining methods, for example, an Alizarin Red (AR) staining method and a von Kossa (VK) staining method. The results are shown in FIG. 9A.

Figure 9:
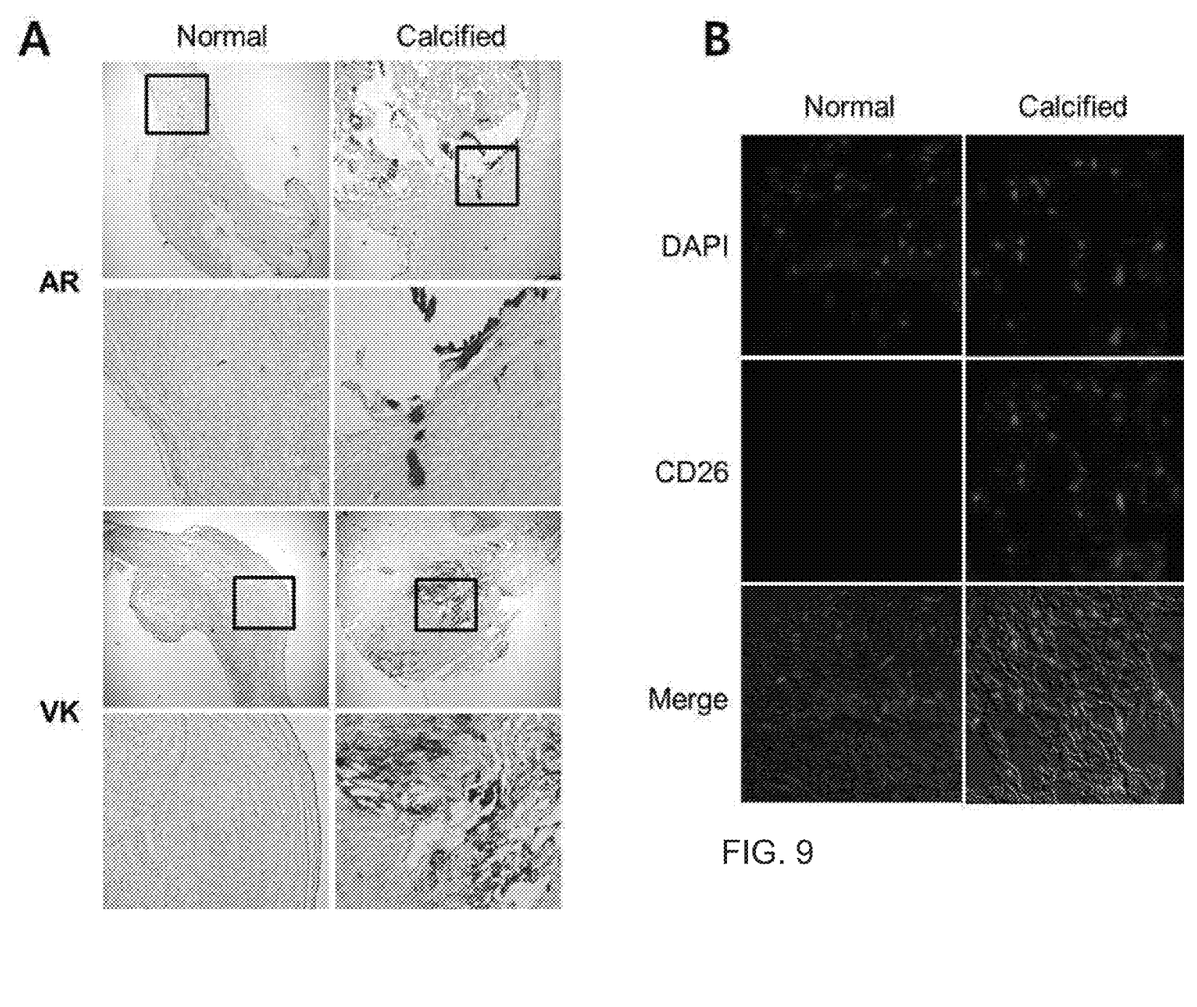
FIG. 9 is a diagram showing the results obtained by determining the correlation between valve tissue calcification and CD26 expression in the aortic valve disease patients according to still another exemplary embodiment of the present disclosure.

As shown in FIG. 9A, the calcification was not detected in the tissues of the normal group, whereas the calcification was detected at an increased level in the tissues of the patient group.

A fluoroimmunoassay was also used to determine an expression level of CD26 in aortic valve disease patients. More particularly, heart valve tissues were obtained from aortic valve disease patients, and fixed. Thereafter, CD26 of the tissues was bound to an anti-CD26 primary antibody after fragmentation, and then labeled with red fluorescence by means of a secondary antibody labeled with an Alexa 649 fluorescent marker capable of specifically binding to the primary antibody. The cell nuclei in the tissues were stained with a fluorescent marker DAPI, and the two fluorescent markers were observed under a confocal microscope. The results are shown in FIG. 9B.

As shown in FIG. 9B, it was revealed that the CD26 was expressed at an increased level in the tissues of the patient group, compared to the tissues of the normal group in which the calcification did not occur.

Example 10

Determination of Promotion of Ossification of Vascular Smooth Muscle Cells by CD26

For the wild-type mice and eNOS KO mice, it was determined whether the promotion of ossification of vascular smooth muscle cells was induced by CD26 using an ALP staining method as a staining method used at the initial calcification stage, an AR staining method as a staining method used at the middle calcification stage, and a VK staining method as a staining method used at the late calcification stage. The results are shown in FIG. 10A.

Figure 10:
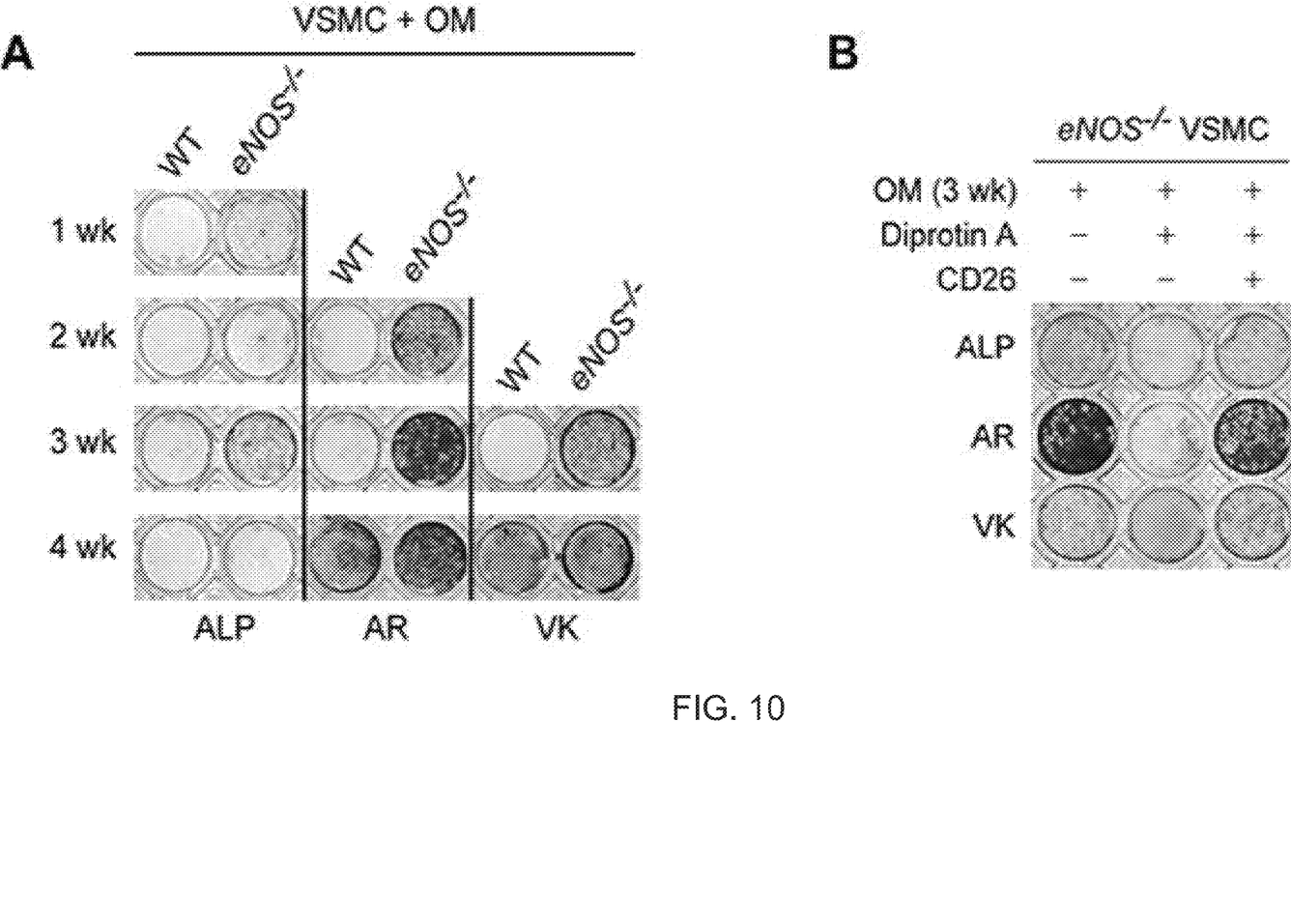
FIG. 10 is a diagram showing the results obtained by determining the promotion of ossification of vascular smooth muscle cells by CD26 according to still another exemplary embodiment of the present disclosure.

As shown in FIG. 10A, it was revealed that the osteogenic differentiation of the vascular smooth muscle cells (VSMC) was promoted in the eNOS KO transgenic mice, compared to the control mice.

Also, the vascular smooth muscle cells from the eNOS KO mice were treated with CD26 and a CD26 inhibitor, diprotin A, respectively. The results are shown in FIG. 10B.

As shown in FIG. 10B, it was revealed that the osteogenic differentiation promoted by the CD26 was inhibited by the CD26 inhibitor.

Example 11

Determination of Decrease in Calcification of Cardioaorta by CD26 Inhibitor

Figure 11:
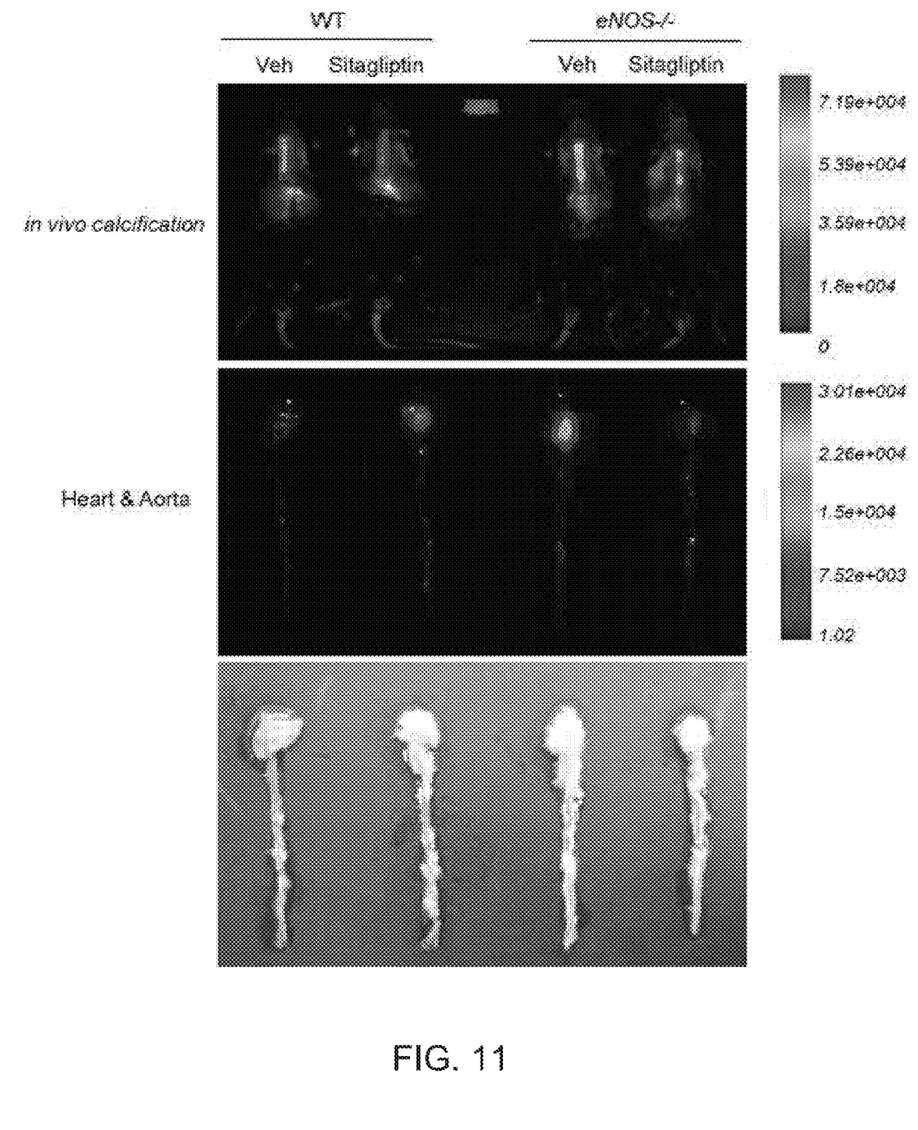
FIG. 11 is a diagram showing the results obtained by determining a decrease in calcification of the cardioaorta by a CD26 inhibitor according to yet another exemplary embodiment of the present disclosure.

To determine whether the calcification of the cardioaorta decreased by the CD26 inhibitor, a CD26 inhibitor drug, DPPIV inhibitor sitagliptin, was administered to the control and the eNOS KO transgenic mice. Thereafter, the intensity of fluorescence was monitored by injecting Osteosense into the mice to check the in vivo calcium deposition. The results are shown in FIG. 11. In FIG. 11, the red intensity of fluorescence represents a level of calcification.

As shown in FIG. 11, it was revealed that the calcification in the cardioaorta slowly proceeded upon administration of the CD26 inhibitor.

As set forth above, according to exemplary embodiments of the present disclosure, the DPP-4 according to one exemplary embodiment of the present disclosure is expressed at an increased level when the blood vessels and valves are calcified, and the calcification decreases remarkably upon administration of the DPP-4 inhibitor. Therefore, the DPP-4 inhibitor can be useful in treatment or prophylaxis of blood vessels or valves.

While exemplary embodiments have been shown and described above, it will be apparent to those skilled in the art that modifications and variations could be made without departing from the spirit and scope of the present invention as defined by the appended claims.

What is claimed is:

1. A method for inhibiting aortic valvular calcification in a subject with valvular disease, the method comprising treating said subject with a pharmaceutical composition comprising a dipeptidyl peptidase-4 (DPP-4) inhibitor.

2. The method according to claim 1, wherein the DPP-4 inhibitor is an inhibitor for inhibiting expression of a DPP-4 nucleotide sequence, or activities of a DPP-4 protein.

3. The method according to claim 2, wherein the inhibitor for inhibiting the expression of the DPP-4 nucleotide sequence is at least one selected from the group consisting of an antisense nucleotide sequence against mRNA of the DPP-4, an aptamer, small interfering RNA (siRNA), short hairpin RNA (shRNA), micro RNA (miRNA), and RNA interference (RNAi).

4. The method according to claim 2, wherein the inhibitor for inhibiting the activities of the DPP-4 protein is at least one selected from the group consisting of an antibody against DPP-4, gliptin, berberine, diprotin, and lupeol.

5. The method according to claim 4, wherein the gliptin is selected from the group consisting of sitagliptin, vildagliptin, saxagliptin, linagliptin, dutogliptin, gemigliptin, alogliptin, anagliptin, Evogliptin, Omarigliptin, teneligliptin, and trelagliptin.

* * * * *